United States Patent
Goerlach-Doht et al.

(10) Patent No.: US 9,693,959 B2
(45) Date of Patent: Jul. 4, 2017

(54) METHOD OF CONTROLLING THE RELEASE OF AN ACTIVE INGREDIENT FROM A DOSAGE FORM

(75) Inventors: Yvonne M. Goerlach-Doht, Rosengarten (DE); Juergen Hermanns, Nottensdorf (DE); Nicholas S. Grasman, Midland, MI (US)

(73) Assignee: Dow Global Technologies LLC

( * ) Notice: Subject to any disclaimer, the term of this patent is extended or adjusted under 35 U.S.C. 154(b) by 1261 days.

(21) Appl. No.: 13/156,889

(22) Filed: Jun. 9, 2011

(65) Prior Publication Data

US 2012/0029091 A1 Feb. 2, 2012

Related U.S. Application Data

(60) Provisional application No. 61/368,432, filed on Jul. 28, 2010.

(51) Int. Cl.
*A61K 47/38* (2006.01)
*A61K 9/20* (2006.01)
*A61K 9/14* (2006.01)
*A61K 31/192* (2006.01)

(52) U.S. Cl.
CPC ............ *A61K 9/2054* (2013.01); *A61K 9/146* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 2,262,155 A * | 11/1941 | Andrews | 425/422 |
| 4,734,285 A | 3/1988 | Alderman | |
| 4,979,681 A | 12/1990 | Doenges et al. | |
| 6,320,043 B1 | 11/2001 | Weber et al. | |
| 6,509,461 B2 | 1/2003 | Schlesiger et al. | |
| 7,259,257 B2 | 8/2007 | Schlesiger et al. | |
| 2001/0034441 A1 | 10/2001 | Schlesiger et al. | |
| 2011/0104270 A1 | 5/2011 | Yanagi et al. | |

FOREIGN PATENT DOCUMENTS

| | | | |
|---|---|---|---|
| EP | 0201895 A2 | 11/1986 | |
| GB | 2262527 A * | 6/1993 | ............. C08B 11/20 |
| JP | 2686215 B2 | 12/1997 | |
| JP | 2007277103 | 10/2007 | |
| WO | 96/00748 | 1/1996 | |
| WO | 00/35295 A1 | 6/2000 | |
| WO | 02/19990 A1 | 3/2002 | |
| WO | 2008127794 A2 | 10/2008 | |

OTHER PUBLICATIONS

Lapidus et al., J. Pharma. Sci. 57, 1292-301 (1968).*
Masaaki Sugimoto, et al., "Improvement of Dissolution Characteristics and Bioavailability of Poorly Water-Soluble Drugs by Novel Cogrinding Method using Water-Soluble Polymer", International Journal of Pharmaceutics, vol. 160, No. 1, Jan. 12, 1998.
Ullmann's Encyclopedia of Industrial Chemistry, Fifth Completely Revised Edition, vol. A5, 1986, p. 1-29.
Houben-Weyl, "Methods of Organic Chemistry", 4th Edition, vol. E20, (1987), p. 2042-2094.
Witt, et al., Direct Imaging of Very Fast Particles Opens the Application of the Powerful (Dry) Dispersion for Size and Shape Characterization, Sympatec GmbH, 2004, p. 1-4.

* cited by examiner

*Primary Examiner* — Theodore R West

(57) ABSTRACT

A method of controlling or adjusting release of an active ingredient from a dosage form comprising the active ingredient and a polysaccharide derivative has been found. The method comprises the steps of
a) providing a composition comprising a polysaccharide derivative and a controlled amount of a liquid diluent, based on the dry weight of the polysaccharide derivative,
b) subjecting the composition to a dry-grinding operation to provide a dry-ground polysaccharide derivative, and
c) incorporating the dry-ground polysaccharide derivative and an active ingredient into a dosage form.

2 Claims, No Drawings

METHOD OF CONTROLLING THE RELEASE OF AN ACTIVE INGREDIENT FROM A DOSAGE FORM

CROSS-REFERENCE TO RELATED APPLICATION(S)

This application claims benefit of priority from U.S. Provisional Application No. 61/368,432, filed Jul. 28, 2010, which application is incorporated by reference herein in its entirety.

This invention relates to a method of controlling or adjusting release of an active ingredient from a dosage form comprising the active ingredient.

BACKGROUND OF THE INVENTION

Sustained release dosage forms have found wide usage in a variety of technology areas, such as in personal care or agricultural applications, water treatment and particularly in pharmaceutical applications. Sustained release dosage forms are designed to release a finite quantity of a compound into an aqueous environment over an extended period of time. Known sustained release pharmaceutical dosage forms contain a medicament or a vitamin whose rate of release is controlled by a polymeric matrix. Sustained release pharmaceutical dosage forms are desirable because they provide a method of delivering a long-lasting dose in a single application without overdosing. U.S. Pat. No. 4,734,285 discloses that the release of an active composition from a solid tablet can be prolonged by employing a fine particle sized hydroxypropyl methylcellulose ether composition. The particle size of the hydroxypropyl methylcellulose ether is so small that at least 90 percent by weight of the cellulose ether particles pass through a 100 mesh screen, and preferably at least 97 percent by weight of the cellulose ether particles pass through a 140 mesh screen to achieve a long release profile. The fine particle size of the hydroxypropyl methylcellulose ether compositions can be achieved using a ball mill for grinding the hydroxypropyl methylcellulose ether compositions. While excellent sustained release profiles are achieved when incorporating the ball milled hydroxypropyl methylcellulose ether into the pharmaceutical dosage form, it is difficult to precisely control the sustained drug release profile using a ball mill. Hydroxypropyl methylcellulose ether batches that do not meet the desired sustained release profile have to be reprocessed or used for other purposes.

Accordingly, it would be desirable to find another way of controlling or adjusting the release of an active ingredient from a dosage form.

SUMMARY OF THE INVENTION

One aspect of the present invention is a method of controlling or adjusting release of an active ingredient from a dosage form comprising the active ingredient and a polysaccharide derivative,
which method comprising the steps of
a) providing a composition comprising a polysaccharide derivative and a controlled amount of a liquid diluent, based on the dry weight of the polysaccharide derivative,
b) subjecting the composition to a dry-grinding operation to provide a dry-ground polysaccharide derivative, and
c) incorporating the dry-ground polysaccharide derivative and an active ingredient into a dosage form.

Another aspect of the present invention is the use of a diluent control in a composition comprising a polysaccharide derivative and a liquid diluent in the range of 0.4 to 50 weight parts of liquid diluent per weight part of dry polysaccharide derivative, prior to a process for dry-grinding the polysaccharide derivative, for controlling or adjusting release of an active ingredient from a dosage form comprising the active ingredient and the polysaccharide derivative.

The amount of liquid diluent, based on the dry weight of the polysaccharide derivative, in a composition comprising the polysaccharide derivative and the liquid diluent is designated hereafter as "diluent load".

Surprisingly, it has been found that there is a correlation, typically a linear correlation, between the diluent load of the polysaccharide derivative prior to dry-grinding and the percentage of active ingredient released over time from a dosage form comprising the active ingredient and the polysaccharide derivative. It has surprisingly been found that a higher diluent load of the polysaccharide derivative prior to dry-grinding leads to a faster release of the active ingredient over time and vice versa. This finding allows the production of polysaccharide derivatives and incorporating them into a dosage form to provide optimal release of the active ingredient over time for a given application.

DETAILED DESCRIPTION OF THE INVENTION

The polysaccharide derivatives utilized in the present invention, preferably the cellulose derivatives, are generally soluble or at least soakable in solvents, preferably water. Preferred polysaccharide derivatives are polysaccharide ethers and polysaccharide esters, more preferably cellulose ethers and esters, most preferably water-soluble cellulose ethers. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the polysaccharides according to the invention are not limited to these groups. Typical polysaccharide derivatives are guar derivatives, starch derivatives, chitin or chitosan derivatives, and preferably cellulose derivatives, but the polysaccharide derivatives according to the invention are not limited to these.

The cellulose derivatives rank among the industrially important polysaccharide derivatives. Their preparation, properties and applications are described, for example, in Ullmann's Encyclopedia of Industrial Chemistry, 5th Edition, (1986), Volume A5, pages 461-488, VCH Verlagsgesellschaft, Weinheim or in "Methoden der organischen Chemie" (methods of organic chemistry), 4th Edition (1987), Volume E20, Makromolekulare Stoffe, Part Volume 3, pages 2048-2076, Georg Thieme Verlag, Stuttgart.

Examples of cellulose derivatives are hydroxyethyl cellulose (HEC), hydroxypropyl cellulose (HPC), ethyl hydroxyethyl cellulose (EHEC), carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydroxypropyl methylcellulose acetate succinate (HPMC-AS), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CM-SEC), hydrophobically modified sulfoethyl cellulose (hm-SEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC). Particularly preferred cellulose derivatives are cellulose ethers having a thermal flocculation point in water, such as, for example, methyl cellulose, methyl hydroxyethyl cellulose, methyl hydroxypropyl cellulose and hydroxypropyl cellulose.

The production of polysaccharide derivatives, preferably polysaccharide ethers and polysaccharide esters is known in the art. Typically the production process involves activating the polysaccharide, such as cellulose, for example by treatment with an alkali metal hydroxide, reacting the thus treated polysaccharide with a derivatizing agent, such as an etherifying or esterifying agent, and washing the polysaccharide derivative to remove by-products. After the washing step the polysaccharide derivative generally has a moisture content of from 30 to 60 percent, typically from 45 to 55 percent, based on the total weight of the moist polysaccharide derivative. While the preferred washing liquor may depend on the specific type of polysaccharide derivative, preferred washing liquors generally are water, isopropanol, acetone, methylethylketone or brine. More preferred washing liquors generally are water or brine. Cellulose derivatives are generally washed at a temperature of from 20 to 120° C., preferably from 65 to 95° C. A solvent-moist, preferably a water-moist filter cake is obtained after washing and separating the polysaccharide derivative from the washing liquor. The moist polysaccharide derivative is usually obtained in the shape of moist granules, moist lumps and/or a moist paste.

In step a) of the method of the present invention a composition is provided which comprises a polysaccharide derivative and a controlled amount of a liquid diluent, based on the dry weight of the polysaccharide derivative. Controlling the diluent load of the polysaccharide derivative prior to dry-grinding is essential. Preferably the release of the active ingredient from a dosage form is controlled and adjusted by controlling and adjusting the amount of the liquid diluent, based on the dry weight of the polysaccharide derivative in step a). The release of the active ingredient from the dosage form at a given time can be adjusted to a first value by a first amount of the liquid diluent, based on the dry weight of the polysaccharide derivative in step a), and the release of the active ingredient from the dosage form at the given time can be adjusted to a second value by a second amount of the liquid diluent, based on the dry weight of the polysaccharide derivative in step a). The diluent load is preferably at least 0.4 weight part, such as kg, of a liquid diluent per weight part, such as kg, solid polysaccharide derivative, more preferably at least 1.0 weight part liquid diluent per weight part solid polysaccharide derivative, and most preferably at least 1.2 weight part liquid diluent per weight part solid polysaccharide derivative prior to dry-grinding. The diluent load is preferably up to 50 weight parts liquid diluent per weight part solid polysaccharide derivative, more preferably up to 10 weight parts, most preferably up to 4.0 weight parts, and particularly up to 2.5 weight parts liquid diluent per weight part solid polysaccharide derivative. The diluent load can be determined by measuring the mass flow of the liquid diluent and the mass flow of the solid polysaccharide. Both mass flows are typically measured in kg per hour. The mass flow of the liquid diluent can be measured using a commercial Coriolis mass flow meter, e.g. as offered by Endress and Hauser, Weil am Rhein, Germany. The mass flow of the solid polysaccharide can be determined using a commercial loss-in-weight feeder, e.g as offered by Brabender Technologie KG, Duisburg, Germany, measuring the dosage of kg solid mass per time unit.

The diluent is liquid at 23° C. and atmospheric pressure. Typically the polysaccharide derivative is contacted with a diluent that dissolves, partially dissolves or soaks the polysaccharide derivative. The polysaccharide derivative is generally contacted with a diluent at a temperature of from 0 to 75° C., preferably from 8 to 75° C., more preferably from 8 to 60° C., most preferably from 15 to 40° C. Suitable diluents are typically diluents whose molecules have polar groups which preferably contain the hetero atoms nitrogen, sulfur or oxygen. However, hydrocarbons and halogenated hydrocarbons may also be used. Preferred diluents are water, alcohols such as methanol, ethanol or isopropanol or esters such as ethyl acetate and butyl acetate. The particularly preferred diluent is water. The term "diluent" as used herein also includes mixtures of diluents.

According to one aspect of the present invention the composition comprising a polysaccharide derivative and a controlled amount of a liquid diluent in step a) is provided by separating a polysaccharide derivative from a suspension thereof in a liquid diluent, such that a controlled amount of liquid diluent remains. The suspension of particles in a liquid diluent can originate from the production and washing the polysaccharide derivative, as described above. Separating a polysaccharide derivative from a suspension can be carried out in a known way, such as centrifugation.

According to another aspect of the present invention the composition comprising a polysaccharide derivative and a controlled amount of a liquid diluent in step a) is provided by mixing a dry polysaccharide derivative and a controlled amount of a liquid diluent, such as water, typically in a compounder. The compounder preferably allows thorough and intense mixing and hydration of the polysaccharide derivative. Useful compounders are, for example, granulators, kneaders, extruders, presses, or roller mills, wherein the mixture of the polysaccharide derivative and liquid is homogenised by applying shear forces and compounding, such as a twin-screw compounder. Co-rotating as well as counter-rotating machines are suitable. So-called divided trough kneaders with two horizontally arranged agitator blades that engage deeply with one another and that perform a mutual stripping action, as in the case of twin-screw compounders are particularly suitable. Suitable single-shaft, continuous kneaders include the so-called Reflector® compounders, which are high performance mixers of modular construction, consisting of a multi-part, heatable and coolable mixing cylinder and a unilaterally mounted blade mixer (manufacturer: Lipp, Germany). Also suitable are so-called pinned cylinder extruders or Stiftconvert® extruders (manufacturer: Berstorff, Germany). The pins incorporated in the housing serve as abutments in order to prevent the kneaded material rotating together with the shaft. Kneader mixers with so-called double-blade sigma stirrers (manufacturer: Fima, Germany) in a horizontal assembly are particularly suitable. The blades operate at different speeds and their direction of rotation can be reversed. A stirred vessel with a vertically arranged mixer shaft is also suitable if suitable flow baffles are mounted on the vessel wall in order to prevent the kneaded mass rotating together with the stirrer shaft, and in this way an intensive mixing action is imparted to the kneaded material (manufacturer: Bayer AG). Also suitable are double-walled mixing vessels with a planetary stirrer and inline homogeniser.

In step b) of the process of the present invention the composition of step a) is subjected to a dry-grinding operation to provide a dry-ground polysaccharide derivative. The composition of step a) is usually in the shape of moist granules, moist lumps and/or a moist paste. Preferably, the composition of step a) is subjected to a dry-grinding operation in a rotational dry-grinding device. The circumferential speed of the dry-grinding device is preferably controlled and optionally varied or adjusted in a range from 35 to 140 m/s, more preferably from 45 to 120 m/s, most preferably from 55 to 115 m/s. Dry-grinding is generally described in the art as drying and grinding simultaneously in one process step with one unit operation. Dry-grinding can be conducted in a known dry-grinding device, for example in a gas-swept impact mill, preferably an air-swept impact mill, wherein the polysaccharide derivative is subjected to an impacting and/or shearing stress. Suitable mills are, for example, hammer mills, screen-type mills, pin mills, disk mills, jet mills, or preferably classifier mills. Drying is typically accomplished with a combination of hot gas and mechanical energy. Hot air is most commonly used but also hot nitrogen gas can be used. The hot gas and the wet product stream are generally fed via separate inlets into the mill, typically hot gas from the bottom and wet product at a side entrance via a feed screw system connected to the mill.

Alternatively, superheated vapor of a solvent, such as superheated steam, or a steam/inert gas mixture or a steam/air mixture can be used as heat-transfer gas and transport gas, as described in more detail in European Patent Applications EP 0 954 536 A1 (equivalent to U.S. Pat. No. 6,320,043), EP-A 1 127 895 (equivalent to U.S. Pat. No. 6,509,461) and EP 1 127 910 A1. In the dry-grinding step b) of the method of present invention the moisture content of the polysaccharide derivative after dry-grinding is typically reduced to an amount of 0.01 to 0.25 weight parts, preferably 0.01 to 0.1 weight parts, more preferably 0.01 to 0.05 weight parts of liquid diluent per weight part of dry polysaccharide derivative.

A preferred method of controlling or adjusting release of an active ingredient from a dosage form comprising the active ingredient and a polysaccharide derivative comprises the steps of
a) providing at least two compositions, preferably at least 3 compositions, more preferably at least 4 compositions, most preferably at least 8 compositions, each comprising a polysaccharide derivative and a different controlled amount of a liquid diluent, based on the dry weight of the polysaccharide derivative,
b) subjecting each composition to a dry-grinding operation to provide a dry-ground polysaccharide derivative from each composition, and
c) incorporating each dry-ground polysaccharide derivative and an active ingredient into a separate dosage form,
d) determining the release of the active ingredient from the dosage form, typically at specific time intervals, for example after 0.5 hours, 1 hour, 2, 3, 4, 5, 6, 7, 8, 9, 10, 11, 12, 13, 14, 15, 16, 17, 18, 19, 20, 21, 22, 23 and/or 24 hours,
e) establishing the correlation between i) the release of the active ingredient from the each dosage form and ii) the weight ratio between the liquid diluent and the polysaccharide derivative, based on its dry weight, in the composition of step a), and
f) utilizing the established correlation to adapt the amount of liquid diluent in the composition of step a) to the desired release of the active ingredient from the dosage form.

After dry-grinding the polysaccharide derivative preferably has a median particle length of at least 50 micrometers, more preferably at least 60 micrometers, and most preferably at least 70 micrometers. The polysaccharide derivative preferably has a median particle length of up to 2000 micrometers, more preferably up to 600 micrometers, and most preferably up to 350 micrometers. The length of the particle is defined as the longest direct distance between opposite ends of the particle inside the particle contour, designated as LOP (Length of Particle). "Direct" means without loops or branches. The LOP is preferably measured by a high speed image analysis system which combines particle size and shape analysis. This specific image analysis method is described in: W. Witt, U. Köhler, J. List, Current Limits of Particle Size and Shape Analysis with High Speed Image Analysis, PARTEC 2007.

The LOP (50,3) is the median length and is defined as follows: All particle size distributions, e.g. the LOP can be displayed and applied as number (0), length (1), area (2) or volume (3) distribution. Preferably the volume distribution of the LOP is calculated as cumulative distribution $Q_3$. The volume distribution within the particle length value LOP 50,3 is designated by the number 3 after the comma. The designation 50, reflecting the median value, stands for 50% of the length of particle distribution being smaller than the given value in μm and 50% being larger. The 50% LOP value is calculated by the image analyzer software. A high speed image analysis system is commercially available from Sympatec GmbH, Clausthal Zellerfeld, Germany as dynamic image analysis (DIA) system QICPIC™. The system analyses the shape of the particles and takes potential curliness of the particles into account. It provides a more accurate measurement of true particle sizes than other methods. The dynamic image analysis (DIA) system QICPIC™ is described in more detail by Witt, W., Köhler, U., List, J.: Direct Imaging of very fast Particles Opens the Application of Powerful (dry) Dispersion for Size and Shape Characterization, PARTEC 2004, Nuremberg, Germany.

In step c) of the method of the present invention the dry-ground polysaccharide derivative and an active ingredient are incorporated into a dosage form. The dry-ground polysaccharide derivative is useful as an excipient for the dosage form, particularly as an excipient for a sustained-release dosage form, which means that it has the function to regulate the release of an active ingredient from the dosage form over an extended period of time. The term "sustained-release" is used herein synonymously to the terms prolonged release; extended release; sustained release; depot release; time release; controlled release; modified release or prolonged action. "Sustained release" is an approach by which active compounds, such as biologically active compounds, are made available at a rate and duration designed to accomplish an intended effect. For example, an oral controlled release drug delivery system is a dosage form that regulates the release of a drug into the gastrointestinal tract, thereby controlling the absorption rate of that drug in order to achieve a desired blood plasma profile. These dosage forms are designed to provide a constant or nearly constant drug level in plasma with reduced fluctuation via a slow, continuous release of drug over an extended period of time. In the sustained-release dosage form of the present invention it generally takes between 0.75 and 36 hours, typically between 4 and 30 hours, and more typically between 8 and 24 hours to release the active ingredient from the dosage form. The polysaccharide derivative is useful as an excipient for dosage forms, particularly for sustained-release dosage forms in a variety of technological fields, for example in personal care, laundry care or agricultural applications, water treatment, and particularly in human or animal health care applications, most specifically pharmaceutical applications wherein a biologically active ingredient is incorporated into a dosage form, particularly one selected from vitamins, herbal and mineral supplements and drug substances.

Before the dry-ground polysaccharide derivative is incorporated into the dosage form, it can be subjected to a granulation step, preferably a wet-granulation step wherein the dry-ground polysaccharide derivative particles are agglomerated by means of a binding liquid. A number of wet-granulation processes are known in the art and are frequently categorized by the magnitude of the shear forces that are exerted on the powder bed being granulated. For example, so-called "low shear granulation" is usually accomplished using planetary mixers, in which vertical mixing blades rotate through the powders at relatively slow speeds. Somewhat greater (i.e., "medium") shear forces can be produced in granulation equipment in which the powders are confined in a cylindrical shell and the powders are agitated in the presence of a granulating liquid, which may or may not contain a binder, by ribbon-type blades. "High shear granulation" is typically performed in equipment in which a main agitator or impeller applies high shear and compaction forces to the powders through the combination of "plowshare" type blades and the relatively high rotation rates at which they move; in addition, the equipment generally also features a smaller, independently controlled, high speed chopper which is designed to break up large lumps produced during the granulation process. The chopper also helps to more fully incorporate the granulating liquid into the material as it is introduced to the mixing vessel, typically through a spray nozzle. A specific type of high shear granulators is referred to as "Lödige granulators" after the name of the first commercial equipment. The Lödige granulators are provided with specially-designed ploughshare blades and high-speed choppers. Another useful wet-granulation process is fluid bed granulation, also called fluidized bed granulation. In this process a binding liquid is sprayed into or on a bed of fluidized powder. Preferably the binding liquid is atomized by compressed air, for example in a binary nozzle before spraying it into or on the bed of fluidized powder. The powder is fluidized in a known manner, for example by a gas flowing vertically through a distributor plate in the base of a processing vessel. In a wet-granulation step the binding liquid generally is water, an organic solvent or a mixture thereof which optionally comprises a binder or a surfactant. Useful organic liquids are alcohols, preferably monofunctional alcohols, such as ethanol; alkenes, alkanes, halogenated alkenes, halogenated alkanes, ethers, esters or oils, such as paraffin oils, animal oils or vegetable oils. Most preferably, the binding liquid is water. Useful binders or surfactants are known in the art. Their amount, if present, preferably is from 0.5 to 10 percent, more preferably from 1 to 5 percent, based on the weight of the liquid. If a binder is used, it is particularly preferred to use a polysaccharide derivative of the same type as the dry-ground polysaccharide derivative.

The dosage form preferably comprises from 10 to 60 percent, more preferably from 15 to 50 percent, most preferably from 25 to 40 percent, of the dry-ground polysaccharide derivative, based on the total weight of the dosage form. The dosage form can comprise one or more excipients and/or adjuvants in addition to the dry-ground polysaccharide derivative. It is to be understood that one or more types of the dry-ground polysaccharide derivative and one or more types of an active ingredient can be blended with one or more optional adjuvants to prepare a dosage form. Preferably the blending process is conducted at about room temperature.

A large variety of active ingredients are useful, dependent on the intended end-use of the dosage form. Active ingredients are known in the art and include, among others, detergents or surfactants for laundry care applications; fertilizers, herbicides or pesticides in formulations designed to release the active ingredient over a prolonged period of time in agricultural applications. A wide range of biologically active ingredients are useful, such as vitamins, herbals and mineral supplements and drugs. The biologically active ingredient includes hydrophobic, hydrophilic and amphiphilic compounds. The biologically active ingredient may be used for treating indications such as, by way of example and without limitation, inflammation, gout, hypercholesterolemia, microbial infection, AIDS, tuberculosis, fungal infection, amoebic infection, parasitic infection, cancer, organ rejection, diabetes, heart failure, arthritis, asthma, pain, congestion, urinary tract infections, vaginal infection, seizure-related disorders, depression, psychosis, convulsion, diabetes, blood coagulation, hypertension and birth control. The amount of the active ingredient generally is at least 0.5 percent, preferably at least 1 percent, more preferably at least 5 percent, most preferably at least 10 percent, based on the total weight of the dosage form, and generally up to 75 percent, preferably up to 65 percent, more preferably up to 55 percent, most preferably up to 45 percent, based on the total weight of the dosage form. The active ingredient is generally solid.

Useful optional adjuvants are known in the art and are generally solid, such as one or more fillers, pigments, colorants, flavorants, disintegrating agents, binders, plasticizers, salts, acidic and basic pH modifiers, antioxidants and/or lubricants. Examples of such adjuvants are acacia, corn starch, guar gum, potato starch, alginic acid, stearic acid, magnesium stearate, lactose, sucrose, dicalcium phosphate, microcrystalline cellulose, sugars, minerals, cellulose powder or cellulose fibers.

The blend of the dry-ground polysaccharide derivative with an active ingredient, and, if desired, with one or more optional adjuvants can be processed to a dosage form, preferably it can be pressed to a tablet in a known manner. The dry-ground polysaccharide derivative preferably forms at least a portion of the matrix of a dosage form.

The present invention is further illustrated by the following Examples which are not to be construed to limit the scope of the invention. Unless otherwise indicated, all parts and percentages are by weight.

Examples 1-18

A commercially available continuous compounder was used to add water to dry METHOCEL™ K100M cellulose ether (CE), commercially available from The Dow Chemical Company. The compounder jacket was supplied with a fluid of −1.3 to 3° C., as shown in Table 1.

METHOCEL™ K100M cellulose ether having a degree of substitution of methoxyl groups of 19-24% and of hydroxypropoxyl groups of 7-12%, a viscosity of 100,000 mPa.s, measured as a 2 percent aqueous solution at 20° C., and a moisture level of 4.6% was fed continuously at a feed rate of listed in Table 1 into the compounder. Water of a temperature of 0 to 10° C., as listed in Table 1, was continuously added at the rates listed in Table 1 to the compounder resulting in 0.950-8.900 kg water load/kg solid cellulose ether, as listed in Table 1. The wet product was transported continuously via a transport belt into a mill feed unit (Altenburger Maschinen Jaeckering GmbH, Hamm, Germany). The bottom blades of the vessel agitator pressed the paste into a single augur screw mounted at the bottom of the vessel. The wet product was forced through a perforated plate directly into the side of an Ultrarotor II "S" impact mill (Altenburger Maschinen Jaeckering GmbH, Hamm, Germany) between the first and second grinding stage. The mill was equipped with 7 grinding stages. The bottom 3 grinding stages were equipped with standard grinding bars. Turbobars were installed in the top 4 grinding stages. A co-rotating finger sifter wheel with 12 blades was installed on the top of the 7th grinding stage. The interior of mill jacket had the standard Altenburger corrugated stationary grinding plates.

The rotor of the impact mill was operated at a circumferential speed of 114 m/s. A hot gas stream, i.e. nitrogen was fed with 994-1435 m$^3$/h into the bottom gas inlet of the mill. A cyclone was used to separate the dried product from the nitrogen. The final product moisture was smaller than 3% by weight.

The controlled drug release performance using a Ketoprofen ("Keto") dosage form was determined after 3, 6, 12, and 20 hours. The ketoprofen formulation was prepared by blending 20 parts ketoprofen (USP), 49 parts impalpable lactose and 15 parts METHOCEL™ K100M, that had been subjected to the procedure described above, for 10 minutes in a Turbula jar blender. An additional 1 part magnesium stearate was added, followed by an additional 1 minute of blending. The resulting formulated system was fed into a Manesty BETA tablet press with 13/32 FFBE tooling and compressed under 5000 lbs (22.5 kN) compression force to produce 400 mg tablets. Tablets were allowed to relax for 24 hours before testing. A USP Type II dissolution apparatus was used to determine drug release performance. The paddle stirring rate was set to 50 RPM and the dissolution media, maintained at 37° C., was 0.05M phosphate buffer at a pH of 5.8. Detection of dissolved ketoprofen was achieved using ultraviolet absorption spectrometry at a wavelength of 260 nm. The results are listed in Table 1 below.

The results in Table 1 illustrate the correlation between the water load of the particulate polysaccharide derivative prior to dry-grinding and the controlled drug release performance using Ketoprofen which was determined after 3, 6, 12, and 20 hours.

The controlled drug release performance after 3 hr using Ketoprofen shows a correlation to the water load according to the formula:

Keto % Released 3 hr=6.6962055+1.5215067*Water Load prior to dry-grinding (kg water/kg CE) with an $R^2$ of 0.888 and a positive slope, i.e. the Ketoprofen % released after 3 hours increases with increasing water load prior to dry-grinding.

Keto % Released 6 hr=12.36661+2.3623837*Water Load prior to dry-grinding (kg water/kg CE) with an $R^2$ of 0.903 and a positive slope, i.e. the Ketoprofen % released after 6 hours increases with increasing water load prior to dry-grinding.

Keto % Released 12 hr=24.788987+3.4189752*Water Load prior to dry-grinding (kg water/kg CE) with an $R^2$ of 0.913 and a positive slope, i.e. the Ketoprofen % released after 12 hours increases with increasing water load prior to dry-grinding.

Keto % Released 20 hr=41.025681+3.7910532*Water Load prior to dry-grinding (kg water/kg CE) with an $R^2$ of 0.896 and a positive slope, i.e. the Ketoprofen % released after 20 hours increases with increasing water load prior to dry-grinding.

What is claimed is:

1. A method of controlling or adjusting release of an active ingredient from a dosage form comprising the active ingredient and a polysaccharide derivative, which method comprises the steps of
   a) providing a composition comprising a polysaccharide derivative and a controlled amount of a liquid diluent, based on the dry weight of the polysaccharide derivative,
   b) subjecting the composition to a dry-grinding operation to provide a dry-ground polysaccharide derivative, and
   c) then combining the dry-ground polysaccharide derivative and an active ingredient, and incorporating them into a dosage form,

TABLE 1

| Example | Water Load prior to dry-grinding (kg Water/ kg CE) | Feed Rate CE (kg/h) | Feed Rate Water (kg/h) | Water Temperature (° C.) | Jacket Temperature (° C.) | Nitrogen Flow (m$^3$/h) | Keto % Released after 3 hr | Keto % Released 6 after hr | Keto % Released after 12 hr | Keto % Released after 20 hr |
|---|---|---|---|---|---|---|---|---|---|---|
| Sample 1  | 0.950 | 30.3 | 28.8  | 2.0 | -1.0 | 1435.0 | 8.8  | 16.1 | 30.3 | 45.9 |
| Sample 2  | 1.000 | 30.0 | 30.0  | 3.0 | -1.0 | 1032.0 | 8.4  | 15.1 | 28.7 | 44.8 |
| Sample 3  | 1.133 | 30.0 | 34.0  | 9.8 |  0.2 | 1063.0 | 8.2  | 14.8 | 28.7 | 45.8 |
| Sample 4  | 1.167 | 30.0 | 35.0  | 2.0 | -1.0 | 1077.0 | 8.7  | 15.2 | 29.3 | 46.6 |
| Sample 5  | 1.167 | 60.0 | 70.0  | 2.0 | -1.0 | 1053.0 | 9.2  | 16.5 | 30.9 | 48.1 |
| Sample 6  | 1.220 | 20.0 | 24.4  | 2.0 | -1.0 | 1069.0 | 8.9  | 16.0 | 30.2 | 47.0 |
| Sample 7  | 1.220 | 10.0 | 12.2  | 5.6 | -1.0 | 1100.0 | 7.9  | 14.2 | 27.2 | 44.5 |
| Sample 8  | 1.220 | 30.0 | 36.6  | 6.0 | -1.0 | 1030.0 | 7.8  | 14.0 | 26.9 | 43.9 |
| Sample 9  | 1.400 | 30.0 | 42.0  | 9.4 |  0.0 | 1053.0 | 8.7  | 15.7 | 29.7 | 46.7 |
| Sample 10 | 1.860 | 10.0 | 18.6  | 5.0 | -1.0 | 1100.0 | 8.4  | 15.5 | 31.0 | 50.8 |
| Sample 11 | 1.957 | 30.0 | 58.7  | 6.3 | -0.8 | 1020.0 | 8.9  | 15.5 | 30.4 | 48.5 |
| Sample 12 | 2.135 | 30.3 | 64.7  | 5.2 |  3.0 | 1032.0 | 11.4 | 20.1 | 36.4 | 53.7 |
| Sample 13 | 2.310 | 30.0 | 69.3  | 0.0 |  0.0 | 1064.0 | 7.9  | 14.5 | 28.0 | 44.4 |
| Sample 14 | 2.937 | 30.3 | 89.0  | 5.2 | -1.0 | 1403.0 | 12.8 | 20.9 | 35.9 | 51.9 |
| Sample 15 | 3.000 | 30.0 | 90.0  | 3.3 | -1.3 | 1017.0 | 11.8 | 19.7 | 33.7 | 48.4 |
| Sample 16 | 3.600 | 30.0 | 108.0 | 5.0 | -1.0 | 1061.0 | 13.8 | 22.4 | 36.8 | 51.6 |
| Sample 17 | 5.600 | 10.0 | 56.0  | 8.2 | -0.8 | 1000.0 | 13.5 | 23.2 | 41.0 | 60.0 |
| Sample 18 | 8.900 | 30.0 | 267.0 | 0.0 |  0.0 |  994.0 | 20.6 | 34.3 | 57.5 | 78.1 | wherein the release of the active ingredient from the dosage form is controlled and adjusted by controlling and adjusting the amount of the liquid diluent, based on the dry weight of the polysaccharide derivative in step a), and wherein the polysaccharide derivative is selected from the group consisting of methyl cellulose, methyl hydroxyethyl cellulose, methyl hydroxypropyl cellulose and hydroxypropyl cellulose, and wherein the release of the active ingredient from the dosage form at a given time is adjusted to a first value by a first amount of the liquid diluent, based on the dry weight of the polysaccharide derivative in step a), and the release of the active ingredient from the dosage form at the given time is adjusted to a second value by a second amount of the liquid diluent, based on the dry weight of the polysaccharide derivative in step a).

2. A method of controlling or adjusting release of an active ingredient from a dosage form comprising the active ingredient and a polysaccharide derivative, which method comprises the steps of a) providing a composition comprising a polysaccharide derivative and a controlled amount of a liquid diluent, based on the dry weight of the polysaccharide derivative, b) subjecting the composition to a dry-grinding operation to provide a dry-ground polysaccharide derivative, and c) then combining the dry-ground polysaccharide derivative and an active ingredient, and incorporating them into a dosage form, wherein the release of the active ingredient from the dosage form is controlled and adjusted by controlling and adjusting the amount of the liquid diluent, based on the dry weight of the polysaccharide derivative in step a), and wherein the polysaccharide derivative is selected from the group consisting of methyl cellulose, methyl hydroxyethyl cellulose, methyl hydroxypropyl cellulose and hydroxypropyl cellulose, and wherein the amount of the liquid diluent is controlled in such an amount that the composition in step a) comprises from 0.4 to 50 weight parts of the liquid diluent per weight part of dry polysaccharide derivative, and the composition is subjected in step b) to a dry-grinding operation to provide a dry-ground polysaccharide derivative comprising from 0.01 to 0.25 weight parts of liquid diluent per weight part of dry polysaccharide derivative.

* * * * *